(12) United States Patent
Burisch et al.

(10) Patent No.: US 9,709,467 B2
(45) Date of Patent: Jul. 18, 2017

(54) METHOD AND APPARATUS FOR DETACHING AND/OR ISOLATING A HISTOLOGICAL SAMPLE

(71) Applicants: Arne Burisch, Braunschweig (DE); Christian Löchte, Braunschweig (DE); Annika Raatz, Braunschweig (DE); Hermann Ulbrich, Bad Schoenborn (DE); Karl-Heinrich Westerhoff, Eppingen (DE)

(72) Inventors: Arne Burisch, Braunschweig (DE); Christian Löchte, Braunschweig (DE); Annika Raatz, Braunschweig (DE); Hermann Ulbrich, Bad Schoenborn (DE); Karl-Heinrich Westerhoff, Eppingen (DE)

(73) Assignee: Leica Biosystems Nussloch Gmbh, Nussloch (DE)

( * ) Notice: Subject to any disclaimer, the term of this patent is extended or adjusted under 35 U.S.C. 154(b) by 461 days.

(21) Appl. No.: 14/477,616

(22) Filed: Sep. 4, 2014

(65) Prior Publication Data

US 2014/0373641 A1 Dec. 25, 2014

Related U.S. Application Data

(62) Division of application No. 13/451,582, filed on Apr. 20, 2012, now Pat. No. 8,850,902.

(30) Foreign Application Priority Data

Apr. 20, 2011 (DE) .......................... 10 2011 002 197

(51) Int. Cl.
 G01N 1/00 (2006.01)
 G01N 1/36 (2006.01)

(52) U.S. Cl.
 CPC ................. *G01N 1/00* (2013.01); *G01N 1/36* (2013.01)

(58) Field of Classification Search
 None
 See application file for complete search history.

(56) References Cited

U.S. PATENT DOCUMENTS

| 4,635,487 A | 1/1987 | Gowing |
| 5,029,484 A | 7/1991 | Somers et al. |

(Continued)

FOREIGN PATENT DOCUMENTS

| GB | 2446920 | 8/2008 |
| GB | 2474549 | 4/2011 |

(Continued)

*Primary Examiner* — Robert R Raevis
(74) *Attorney, Agent, or Firm* — Hodgson Russ LLP

(57) ABSTRACT

The invention relates to an apparatus for treating histological samples, in particular for detaching and/or isolating a histological sample that, in particular after an infiltration operation, is adhering to another sample and/or to the inside of a cassette (1), having a sample receiving chamber (2) which is embodied and intended to be filled at least partly with a liquid (3), in particular with liquid paraffin. The apparatus according to the present invention is characterized in that a displacement means (5) is provided that is introducible into the liquid (3), in particular under open- and/or closed-loop control, in order to elevate the fill level height (6) of the liquid (3), and/or that a displacement means (5) is provided whose volume is increasable, in particular under open- and/or closed-loop control, in order to elevate the fill level height.

3 Claims, 4 Drawing Sheets

(56) References Cited

U.S. PATENT DOCUMENTS

| | | |
|---|---|---|
| 5,415,840 A | 5/1995 | Sano et al. |
| 5,821,115 A | 10/1998 | Graupner |
| 2006/0134732 A1 | 6/2006 | Kram et al. |
| 2010/0055788 A1 | 3/2010 | Ulbrich et al. |
| 2012/0058553 A1 | 3/2012 | Haywood et al. |

FOREIGN PATENT DOCUMENTS

| | | |
|---|---|---|
| WO | 0036393 | 6/2000 |
| WO | 2006073910 | 7/2006 |

METHOD AND APPARATUS FOR DETACHING AND/OR ISOLATING A HISTOLOGICAL SAMPLE

CROSS REFERENCE TO RELATED APPLICATIONS

This application is a divisional application of U.S. patent application Ser. No. 13/451,582 filed on Apr. 20, 2012, which claims priority of German patent application number 10 2011 002 197.3 filed Apr. 20, 2011, the entire disclosures of which are incorporated by reference herein.

FIELD OF THE INVENTION

The invention relates to a method for detaching and/or isolating a histological sample that, in particular after an infiltration operation, is adhering to another sample and/or to the inside of a cassette, for example as a result of solidification of the embedding medium.

The invention further relates to an apparatus for treating histological samples, in particular for detaching and/or isolating a histological sample that, in particular after an infiltration operation, is adhering to another sample and/or to the inside of a cassette, having a sample receiving chamber which is embodied and intended to be filled at least partly with a liquid, in particular with liquid paraffin.

BACKGROUND OF THE INVENTION

In the context of the conditioning of histological samples for later microtoming, in particular in the preparation of histological samples in the context of an embedding process, they are firstly fixed by the application of various chemicals. The tissue liquid originally present in the natural cavities of the sample is thereby replaced, in multiple steps, by a fixing liquid, for example by formalin. In order to convert the fixed samples into a state that permits sectioning by means of a microtome, the fixing liquid is replaced by an embedding medium, for example paraffin, gelatin, agar, nitrocellulose, polyester wax, polyethylene glycol, or plastic. During the aforementioned processes, the samples are usually located in a cassette that comprises a plurality of sieve-like openings so that the chemicals can flow around the samples. A particular embodiment of such a cassette is known, for example, from DE 43 33 118 A1.

After infiltration of the embedding medium into the samples, the excess paraffin is drained off. After this step, the samples can be located anywhere within the cassette; because of the paraffin residues adhering to them, the samples as a rule adhere to the cassette cover, in the cassette cavity, and/or to one another.

Before further processing, in particular for automated, machine-controlled further processing, namely casting the samples into a paraffin block (called "blocking"), the samples must be separated and removed from the cassette. In order to allow the samples to be separated from one another and removed from the cassette, the paraffin that causes the aforementioned adhesion must be melted again. For this, the cassette (in the closed state or in the flipped-open state) can be introduced into a paraffin bath. This must occur largely without jolting. In addition, contamination and functional impairment due to solidifying paraffin must be avoided.

DE 10 2008 039 875 A1 discloses a method and an apparatus for infiltrating tissue samples with paraffin. The apparatus comprises a retort that is embodied as a closable chamber and that can be filled, in valve-controlled fashion via conduits, from a reservoir container of paraffin. For this a vacuum is applied to the closed chamber of the retort so that paraffin is conveyed through the conduit and through special distributors and valves into the retort. In particular because the samples, and the cassette in which the samples are arranged, are not accessible during flooding of the retort, an apparatus of this kind is unsuitable as a paraffin bath for detaching or isolating samples adhering to one another, or samples that are adhering in the interior of a cassette.

SUMMARY OF THE INVENTION

It is an object of the present invention to describe a method that permits detachment or isolation, with as little disruption as possible, of a sample located in a cassette.

The object is achieved by a method which is characterized in that the sample is immobilized in a sample receiving chamber above a first fill level of a liquid, in particular liquid paraffin, that is suitable for counteracting the adhesion; and that the fill level of the liquid is then elevated, in particular under open- and/or closed-loop control, at least until said level reaches the sample.

The further object of the present invention is to describe an apparatus that is usable for detachment and/or isolation, with as little disruption as possible, of a histological sample that, in particular after a infiltration operation, is adhering to another sample and/or to the inside of a cassette.

The object is achieved by an apparatus of the kind cited above which is characterized in that a displacement means is provided which, in order to elevate the fill level height of the liquid, is introducible into the liquid, in particular under open- and/or closed-loop control, and/or that a displacement means is provided whose volume is enlargeable, in particular under open- and/or closed-loop control, in order to elevate the fill level height.

The method according to the present invention has the very particular advantage that a sample can be detached, for example from the cassette cover or from another sample, by targeted setting of the fill level. Advantageously and in accordance with the present invention, the cassette is not, in this context, moved into the liquid, for example into liquid paraffin. Instead the cassette together with the samples located therein, which has been conveyed into the sample receiving chamber, remains at rest, for example in a holder, while the liquid is brought to the cassette and to the samples by raising the liquid level. Unintentional jolting of the cassette and the samples is, in particular, thereby effectively avoided.

In order to detach a sample from the cassette cover, the liquid level can, according to the present invention, firstly be raised until the cassette is completely flooded. The liquid level can then be lowered. The fill level of the liquid can advantageously be set and/or established, in particular after lifting of the cassette cover, so that exclusively the underside of the sample or undersides of the samples is/are wetted with the liquid, so that they cannot adhere to the cassette bottom. With this setting, individual samples can easily be separated from one another inside the cassette, for example using a tweezers, or can be removed from the cassette with a gripper.

The apparatus according to the present invention has the very particular advantage that the fill level height can be set largely arbitrarily and with very high accuracy. In addition, the apparatus according to the present invention has the advantage that contamination, clogging, or sticking of valves or conduits for the liquid is effectively avoided. Instead, the apparatus can be embodied so that neither valves nor conduits that come into contact with the liquid (in particular, with paraffin) are necessary.

The aforesaid advantages make the apparatus according to the present invention ideal for automatic, machine-controlled treatment of histological samples, especially in the context of a fully automatic embedding process, since the apparatus according to the present invention can be embodied in largely maintenance-free or at least extremely low-maintenance fashion.

In an advantageous embodiment of the apparatus, a heating apparatus is provided for heating the sample receiving chamber and/or the liquid, for example paraffin, located in the sample receiving chamber. The heating apparatus can be embodied, for example, as a heating film. The heating apparatus, for example in the form of a heating film, can in particular be arranged effectively and in protected fashion under the sample receiving chamber. In another advantageous embodiment, a heating part that can be immersed into the liquid is provided.

In an advantageous embodiment of the apparatus according to the present invention, the displacement means can be at least partly removed from the liquid, in particular under automatic open- or closed-loop control, in order to decrease the fill level height. Alternatively or additionally, provision can be made according to the present invention that the volume of the displacement means is decreasable, in particular under open- and/or closed-loop control, in order to lower the fill level height.

According to the present invention, the displacement means can in principle exhibit any aggregate state. For example, the displacement means can comprise a fluid and/or can be made up partly of a fluid. In particular, the displacement means can comprise, for example, a flexible and/or extensible casing that can be filled with a fluid in order to elevate the fill level height of the liquid. The fluid can be, for example, a gas or a gas mixture, in particular air. The fluid can also be a displacement liquid.

According to the present invention the fluid can in particular be a displacement liquid that is not miscible with the liquid to be brought into contact with the sample, and does not react with it. An embodiment of this kind can be embodied so that a casing for the displacement liquid can be dispensed with.

In another embodiment, the displacement means is embodied substantially as a solid object, for example as an immersion plunger.

In a very particularly advantageous embodiment of the apparatus according to the present invention, the displacement means has an additional function.

For example, the displacement means can be embodied additionally as a vibration apparatus and/or can contain a vibration apparatus. An embodiment of this kind has the very particular advantage that the sample or samples can be manipulated by the generation of vibrations. For example, samples can be isolated within the chamber as a result of the vibrations, or transported within the cassette (for example, into a grasping position) by targeted selection of the vibration shape and/or vibration parameters.

As an additional function, the displacement means can also, according to the present invention, have a heating function, for example in order to heat the liquid located in the sample receiving chamber. Provision can be made in particular that a heating apparatus is integrated into the displacement means.

In an advantageous embodiment of the apparatus according to the present invention, the sample receiving chamber is embodied in such a way that the samples and/or the cassette located therein is accessible, in particular from above.

In an advantageous embodiment, a fill level sensor is provided. It is particularly advantageous to use a fill level sensor that operates in non-contact fashion, in particular with respect to the liquid. For example, the fill level sensor can be embodied as an ultrasonic sensor. The fill level sensor is preferably embodied and arranged so as to enable a maximally exact determination of the sample receiving chamber fill level of the liquid.

The apparatus according to the present invention can advantageously comprise an open-loop fill level control system or closed-loop fill level control system. Provision can be made in this context, for example, that the extent of the penetration of the displacement means into the liquid and/or the volume of the displacement means is directly or indirectly set as a function of signals of a fill level sensor. An open- or closed-loop fill level control system of this kind can advantageously be implemented on the basis of stored-program electronic modules.

In an advantageous embodiment, a mount for direct and/or indirect, preferably releasable, immobilization of at least one sample and/or one cassette is provided in the sample receiving chamber. Provision can be made in particular that the mount comprises a clip mount and/or a bayonet mount for one or more cassettes. Provision can also be made that the mount comprises a first receptacle for a cassette and a further receptacle for the cover of the cassette. Provision can be made in this context in particular that the bottom of the cassette located in the first receptacle, and the turned-around cover located in the further receptacle, are located in the same horizontal plane.

Further goals, advantages, features, and possible applications of the present invention are evident from the description below of an exemplifying embodiment with reference to the drawings. In this context, all features described and/or graphically depicted, independently or in any useful combination, constitute the subject matter of the present invention, irrespective of their grouping in the claims or their internal references.

BRIEF DESCRIPTION OF THE DRAWING VIEWS

DETAILED DESCRIPTION OF THE INVENTION

Figure 1:
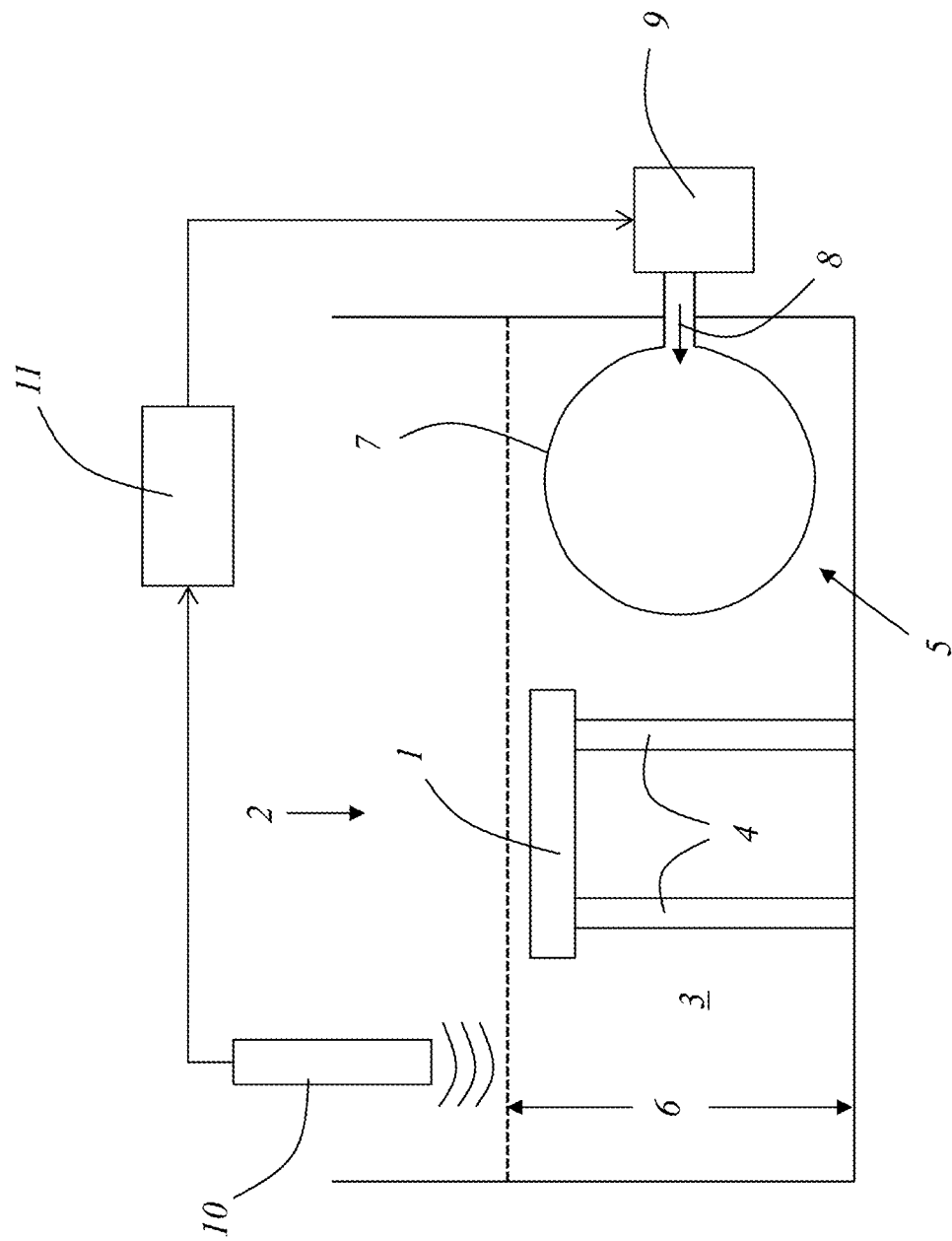
FIG. 1 shows an apparatus according to the present invention having a flexible displacement means, with an elevated fill level.

FIG. 1 shows an apparatus according to the present invention for treating histological samples that are arranged in cassette 1. The apparatus comprises a sample receiving chamber 2 that is embodied and intended to be filled at least partly with a liquid 3, in particular with liquid paraffin.

Cassette 1 is immobilized on a mount 4 by means of a bayonet fastener (not depicted in further detail. The apparatus comprises a displacement means 5 whose volume is enlargeable in regulated fashion in order to elevate fill level height 6. Concretely, displacement means 5 is a balloon-like flexible casing 7 that can be inflated by means of compressed air, as illustrated in the Figure by arrow 8. Inflation of flexible casing 7 causes liquid 3 to be displaced within sample receiving chamber 2 so that fill level height 6 rises.

To decrease fill level height 6, air is released from flexible casing 7. Admission and release of air into flexible casing 7 occurs by means of a valve apparatus 9.

The apparatus comprises a fill level sensor 10, embodied as an ultrasonic sensor, that allows fill level height 6 to be sensed in non-contact fashion. The signals of fill level sensor 10 are forwarded to a fill level height control system 11 that, as a function of the signals of fill level sensor 10, controls valve apparatus 9 in such a way that a predefined or predefinable fill level height 6 is (preferably automatically) established.

Figure 2:
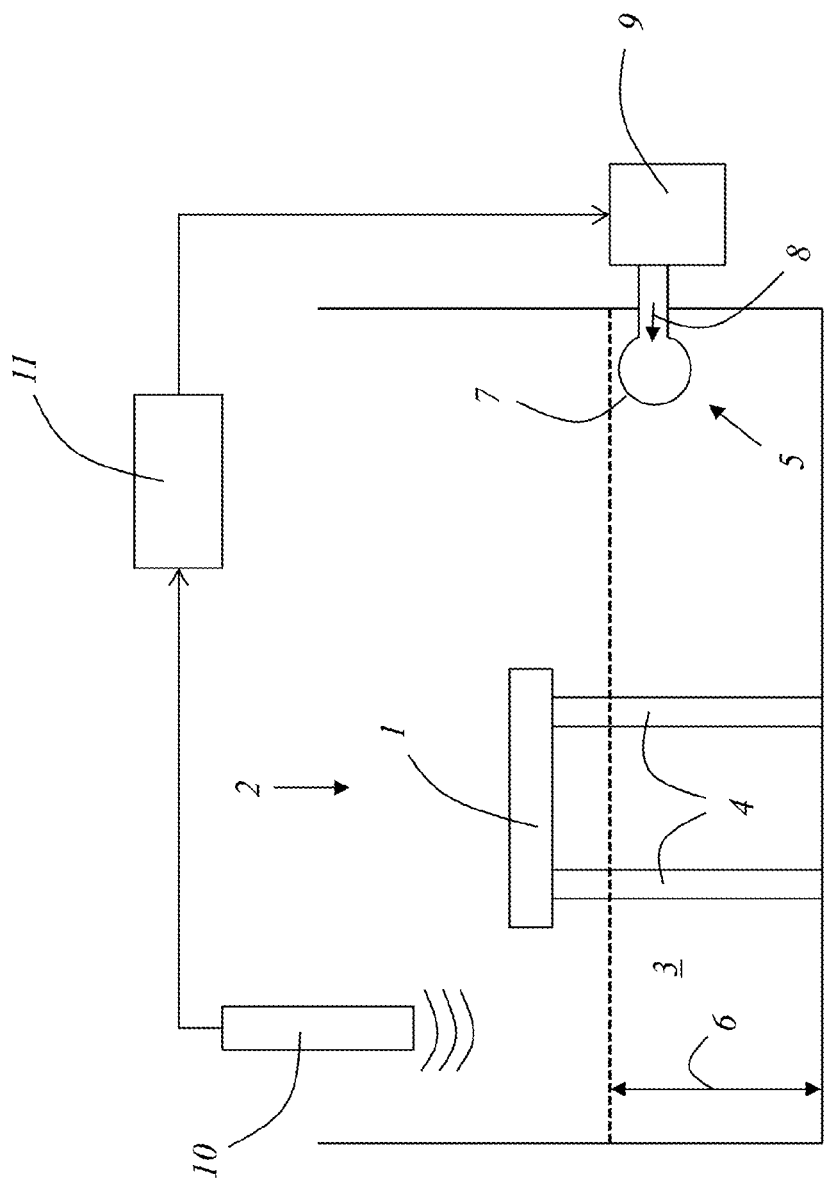
FIG. 2 shows the apparatus according to the present invention with a lowered fill level.

FIG. 2 shows the apparatus according to the present invention with a lowered fill level height 6. This state is, as already discussed, to be brought about by releasing air from flexible casing 7.

Figure 3:
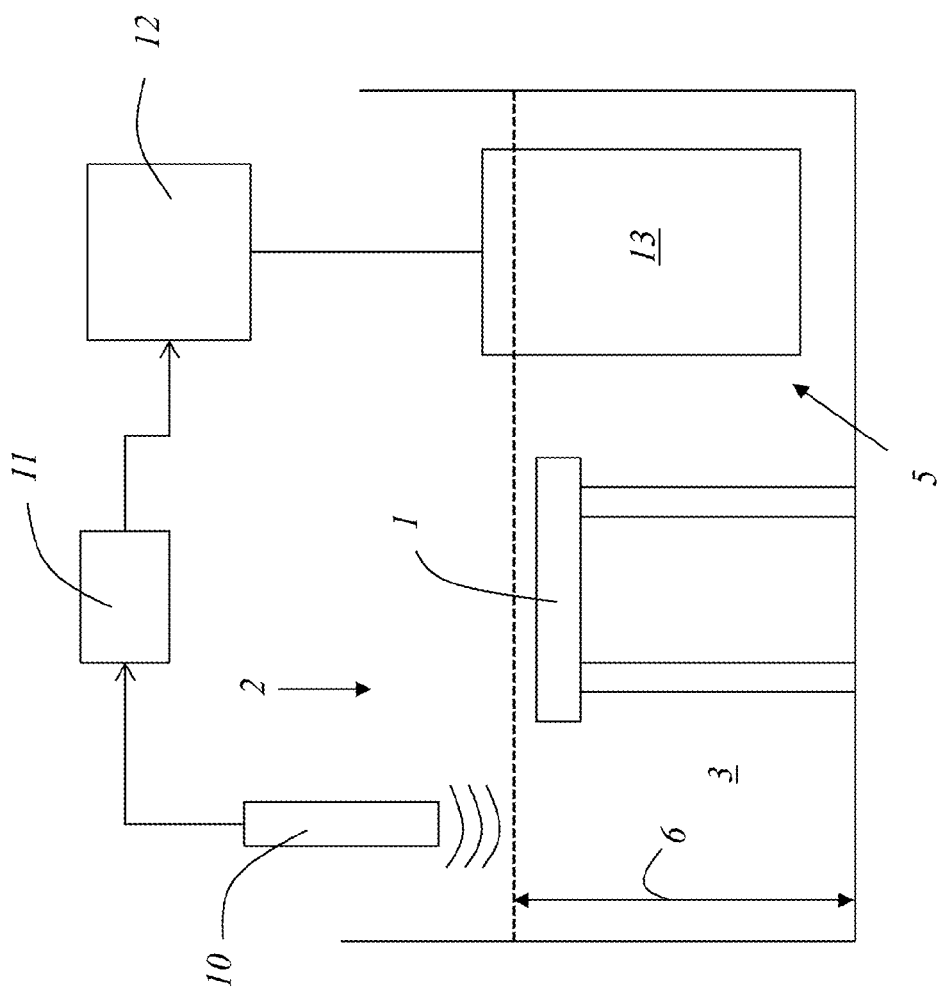
FIG. 3 shows another apparatus according to the present invention with an elevated fill level.

FIG. 3 shows another apparatus according to the present invention for treating histological samples that are arranged in a cassette 1. This apparatus, too, comprises a sample receiving chamber 2 which is embodied and intended to be filled at least partly with a liquid 3, in particular with liquid paraffin. A displacement means 5, namely an immersion plunger 13, which in order to elevate the fill level height of liquid 3 is introduced by an actuation apparatus 12, is provided. To lower liquid level 6, immersion plunger 13 is withdrawn from liquid 3 by actuation apparatus 12. Fill level height 6 can be set in targeted and very accurate fashion by setting the immersion depth of immersion plunger 13. Provided for this purpose is a fill level height control system 11 that receives fill level height signals from a fill level sensor 10 operating in non-contact fashion and, as a function of the received signals, controls actuation apparatus 12 in such a way that a predefined and/or predefinable fill level height 6 is established.

Figure 4:
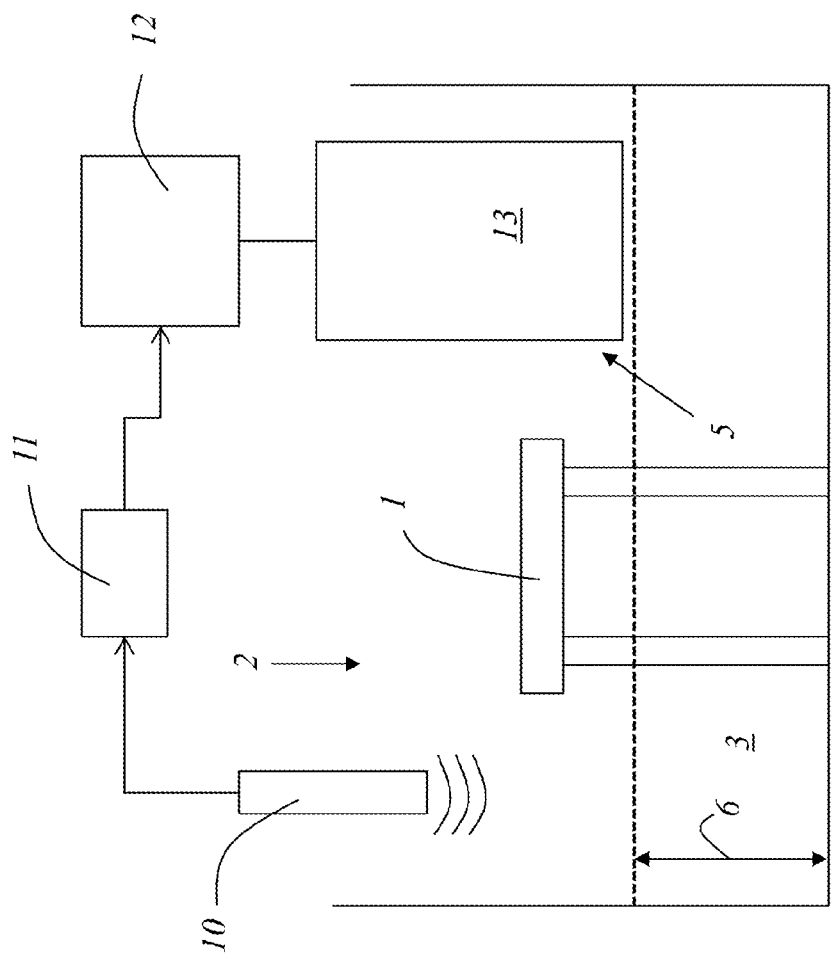
FIG. 4 shows the other apparatus according to the present invention with a lowered fill level.

FIG. 4 shows the apparatus already described with reference to FIG. 3, with a lowered fill level height 6.

PARTS LIST

1 Cassette
2 Sample receiving chamber
3 Liquid
4 Mount
5 Displacement means
6 Fill level height
7 Flexible casing
8 Arrow to illustrate flow of compressed air
9 Valve apparatus
10 Fill level sensor
11 Fill level control system
12 Actuation apparatus
13 Immersion plunger

What is claimed is:

1. A method for detaching and/or isolating a histological sample that is adhering to another sample and/or to the inside of a cassette (1), the method comprising:
    immobilizing the histological sample in a sample receiving chamber (2) above a first fill level of a liquid (3) that is suitable for counteracting the adhesion; and
    elevating the fill level of the liquid (3) after the histological sample is immobilized at least until said fill level reaches the histological sample.

2. The method according to claim 1, wherein the fill level of the liquid (3) is set and/or regulated so that exclusively an underside of the histological sample is wetted with the liquid (3) so that the underside of the histological sample cannot adhere to the cassette bottom.

3. The method according claim 2, wherein the fill level of the liquid (3) is elevated until the cassette (1) is completely flooded.

\* \* \* \* \*